United States Patent [19]

Genyk et al.

[11] 4,453,661
[45] Jun. 12, 1984

[54] SURGICAL INSTRUMENT FOR APPLYING STAPLES

[75] Inventors: Stepan N. Genyk; Vasily M. Krysa; Mikhail V. Zraiko; Ljubomir G. Vovk, all of Ivano-Frankovsk; Ivan I. Pyatiletov, Kiev, all of U.S.S.R.

[73] Assignee: Ivano-Frankovsky Gosudarstvenny Meditsinsky Institut, Ivano-Frankovsk, U.S.S.R.

[21] Appl. No.: 312,748

[22] Filed: Oct. 19, 1981

[30] Foreign Application Priority Data

Oct. 23, 1980 [SU] U.S.S.R. ............................ 2995041
Oct. 23, 1980 [SU] U.S.S.R. ............................ 2995042

[51] Int. Cl.³ .................... B25C 5/04; A61B 17/04
[52] U.S. Cl. .................................. 227/19; 227/70; 227/76; 227/84; 227/DIG. 1; 227/144; 227/145
[58] Field of Search .............. 227/70, 76, 82, 84, 227/85, 86, 87, 88, 90, 91, 92, 93, 94, 97, 142, 143, 144, 155, DIG. 1, 145

[56] References Cited

U.S. PATENT DOCUMENTS

| 477,351 | 6/1892 | Cohen | 227/144 X |
| 715,032 | 12/1902 | Davis | 227/144 X |
| 930,804 | 8/1909 | Skinner | 227/76 |
| 1,174,937 | 3/1916 | Merrick | 227/144 X |
| 1,610,632 | 12/1926 | Svenson | 227/144 X |
| 1,705,819 | 3/1929 | Kruse | 227/85 |
| 3,807,407 | 4/1974 | Schweizer | 227/DIG. 1 |
| 3,842,840 | 10/1974 | Schweizer | 227/DIG. 1 |

FOREIGN PATENT DOCUMENTS

| 1282536 | 12/1961 | France | 227/DIG. 1 |
| 2416682 | 9/1979 | France | . |
| 2014503 | 8/1979 | United Kingdom | . |
| 198514 | 8/1967 | U.S.S.R. | . |
| 300982 | 6/1971 | U.S.S.R. | . |
| 415009 | 7/1971 | U.S.S.R. | . |
| 312024 | 10/1971 | U.S.S.R. | . |
| 419001 | 8/1974 | U.S.S.R. | . |

Primary Examiner—Paul A. Bell
Attorney, Agent, or Firm—Fleit, Jacobson, Cohn & Price

[57] ABSTRACT

A surgical instrument comprises an elongated body provided with a hand lever. At a distal end of said body there is secured a female die having a pit for bending the legs of staples. A clamping jaw provided with a driver for inserting staples is mounted on said body for reciprocating travel in the direction of said female die. Within the clamping jaw there is provided a passage for feeding a wire, and on the clamping jaw there is mounted a knife capable of reciprocating in the direction perpendicular to the outlet end of the conduit, and adapted for cutting wire lengths. On the body there is also mounted a device for forming staples from wire lengths.

15 Claims, 22 Drawing Figures

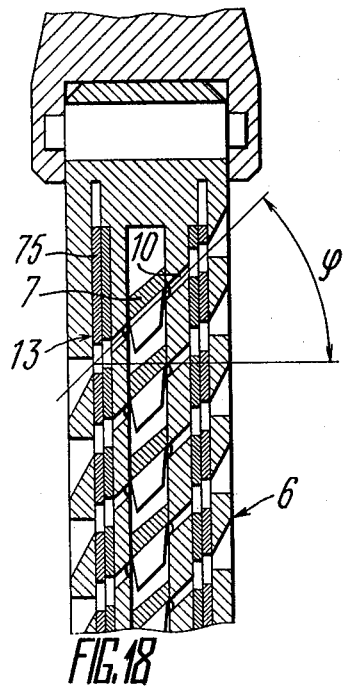
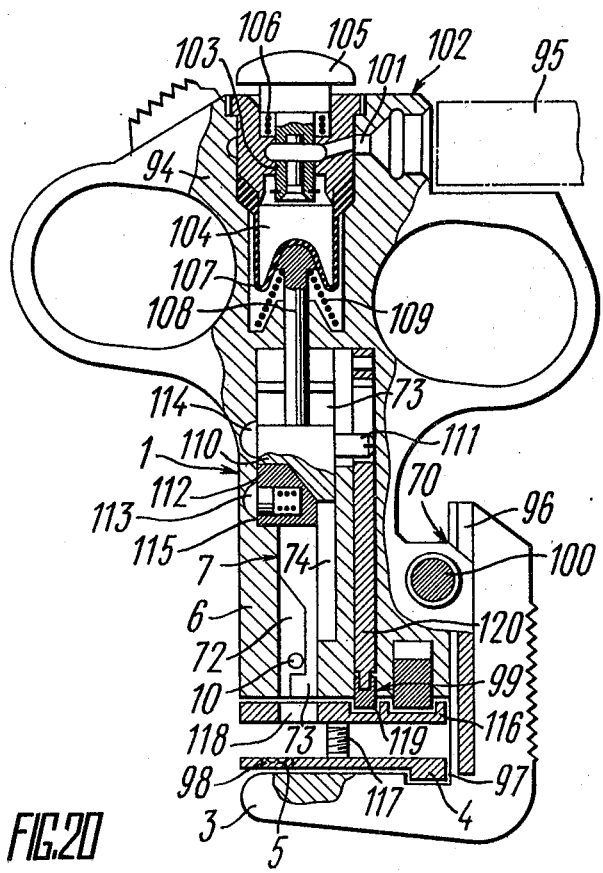
FIG.18
FIG.20

SURGICAL INSTRUMENT FOR APPLYING STAPLES

BACKGROUND OF THE INVENTION

1. Field of the Invention

The present invention relates to medical equipment, and particularly to medical instruments for application of staples.

The invention may prove most advantageous in surgical operations when applying sutures to various organs and soft tissues of an organism.

2. Prior Art

It is known that as far back as 1951, in different countries staples have been used in surgical operations for suturing instead of ligature filaments. This was promoted by such factors as a higher reliability of staple sutures, a decrease in the possibility of occurence of inflammatory processes along the suture line, the prime consideration consisting in simplicity and high rate of suturing with the use of staples. During last 30 years, more than one thousand patents have been granted in the leading countries for various designs of instruments for suturing with staples. Authors of these inventions aspired to reduce dimensions and weight of the instrument and at the same time to decrease unproductive time required by the surgeon to replace or recharge the surgical instrument. Detailed analysis of the prior art demonstrates that up to now this problem has not been solved satisfactorily.

In particular, there is known for a comparatively long time a surgical instrument for suturing with staples (USSR Inventor's Certificate No. 198,514), said instrument being of small dimensions and allowing extremely thin tissues and organ membranes, e.g. cornea, to be joined. The instrument functions simultaneously as a clamp and a suturing device. Its body is constructed as scissors provided with handles and jaws at the ends thereof.

One of the jaws is a clamping jaw and is provided with a socket for mounting a U-shaped staple, while the other jaw carries a female die having pits for bending the staple legs.

It is obvious that in order to apply a lengthy suture, it is necessary to repeatedly install each following staple into the socket of the clamping jaw. In spite of utilization of a special forceps-type gripping instrument, 3 to 5 minutes are required to charge such an instrument with a staple in ophthalmologic operations. It is further obvious that using such instrument for suturing e.g. walls of the stomach under conditions of gastrorrhagia, takes inadmissibly much time despite the fact that charging the instrument with a bigger staple than that used in ophthalmology is significantly simplified. The problem is not solved either by successive utilization of several above mentioned suturing devices, since frequent replacements of the instruments distract the surgeon and are undesirable in complicated operative interventions.

Many attempts have been made to eliminate the above disadvantage. For this end, surgical instruments have been developed having collecting magazines for cartridges whereto a plurality of staples are preliminarily laid (See e.g. USSR Author's Certificates and Patents Nos. 300,982; 312,024; 419,001; British Patent Specification No. 2,014,503; French Patent No. 2,416,682; FRG Patent No. 1,566,175). The bodies of said instruments are constructed in the form either of clips, or scissors. The design concept of the above suturing devices a surgical instrument disclosed in USSR Inventor's Certificate No. 415,009 as an example. This surgical instrument for application of staples comprises an elongated body provided with a hand lever (being a handle in the given instant), a female die having a pit for bending legs of staples, said female die being fastened on a distal end of said body, a clamping jaw provided with a driver for staples and mounted on said body for reciprocating travel in the direction of said female die. On the body there is also mounted a magazine having sockets for staples, said magazine being constructed in the given case as a multicharge drum.

An obvious advantage of such surgical instruments consists in that they enable applying one or several lengthy staple sutures without recharging or replacing the instrument. However, in practice the use of the above instruments is associated sometimes with a number of difficulties and undesirable postoperative effects. At present, a wide range of staples of various sizes is manufactured commercially for such instruments. At the same time, charging the magazines is carried out, as a rule, directly at the medical institutions, and sometimes even in the course of operation. The operation of charging the magazine with diminutive staples required for microsurgical operations, where the size of a staple does not exceed 1.5 mm, requires certain skills, is labor-consuming and takes much time (up to one hour). Besides, there are known cases (which are not guaranteed from their repetition in future), when the magazine was charged by mistake with one or several staples having dimensions close to those required for the given instrument, the former being designed for another special purpose surgical instrument. In some cases this resulted in jamming staples inside the magazine, at the outlet thereof or within the clamping jaw, which caused the interruption of the operation for recharging the magazine or the cartridge. In other cases, when the size of an erroneously charged staple was less than required, it remained unnoticed, however resulting afterwards in the incontinuity of the suture in the postoperative period, in the internal hemorrhages, which may be fatal. Similar negative effects were observed even when the magazine was correctly charged, but at least one staple was damaged while it was being put into the cartridge or the magazine. Such a damage is quite possible since the diameter of a wire used in the manufacture of staples in some cases does not exceed 0.1 mm.

It is also to be noted that the magazine situated close to the clamping jaw causes a substantial increase in the dimensions of the instrument and closes the operative field, thereby complicating the manipulation of the instrument in hard-to-reach places, deep wounds, and sometimes traumatizes tissues or membranes of adjacent internal organs, vessels etc. On the other hand, removal of the magazine or the cartridge from the clamping jaw toward the handlever does not solve this problem either, since it inevitably results in lengthening the path of a staple moving from the magazine toward the driver, and in increasing the possibility of jamming or deforming staples during the operation.

Still another imperfection of the prior art surgical instruments for application of staple sutures consists in their high specialization caused by strictly defined sizes of staples being applied. As it has been previously mentioned, such instruments cannot function when charged with different staples which are not designed for the use therein. For this reason, a great number of special purpose suturing devices similar to those described above, are to be kept in one operative room.

The present invention is directed to the provision of a surgical instrument for application of staples, whose design would permit, at reduced dimensions thereof, to make wire staples being only of a required size, directly when applying a suture, thereby reducing the time required for preparing the instrument, and to eliminate the possibility of errors.

SUMMARY OF THE INVENTION

The main object of the present invention is to provide a surgical instrument for application of staples, ensuring feeding only the staples of a required size to the driver.

Another object of the invention is to reduce the time required for preparing the instrument for operation.

A significant object of the present invention is to lower traumatism of adjacent organs when suturing with staples suture in hard-to-reach places of the operative field.

Still another object of the invention is to increase the convenience of the surgical instrument in operation.

Another object of the present invention is to lower the possibility of occurence of inflammatory processes along the staple suture.

An important object of the present invention is to upgrade the quality of the staple suture.

Still another object of the invention is to provide an instrument permitting rapid formation of lengthy sutures, and at the same time hving comparatively small dimensions.

An additional object of the invention is to upgrade the reliability of the surgical instrument in operation.

Another object of the invention is to eliminate the possibility of jamming the instrument when applying the staple suture.

An important object of the present invention is to provide a multipurpose instrument permitting application of sutures to various organs with utilization of staples of a size required to each specific case.

Another object of the invention is to upgrade strength and reliability of staple sutures without any decrease in flexibility thereof.

Still another object of the present invention is to provide for application of lengthy and curvilinear sutures.

Another object of the invention is to provide a surgical instrument for applying staples, actuated by simple, single-type movements of the control elements.

An important object of the invention is an economically favourable mutual disposition of the elements for controlling the surgical instrument.

The objects set forth and other objects of the present invention are attained by that in a surgical instrument for applying staples, comprising an elongated body provided with a handlever, a female die having a pit for bending the legs of staples and being secured at a distal end of said body, a clamping jaw provided with staple driver and mounted on said body for reciprocating movement in the direction of said female die, according to the invention, within the clamping jaw there is provided a passage for feeding a wire, and on the clamping jaw there is mounted a knife for cutting the wire to the required size, said knife mounted for reciprocating movement in the direction perpendicular to the outlet end of the passage and on the body of the instrument there is also provided a device for forming staples from wire lengths.

The surgical instrument of such a design permits making wire staples of a required size directly while suturing, thereby eliminating the step of charging the magazine, and consequently the possibility of errors as in the case of the prior art. Clinical tests of experimental models of the instrument manufactured in accordance with the invention, have demonstrated that despite widening the functional possibilities of the suturing device, the force required to actuate this device has only slightly increased and doos not exceed allowable limits.

In particular, it has been found that the force required for displacing the knife and cutting off a wire blank in some cases has been even lower than that required for bending staples.

It should be also noted that making the staples during the process of suturing eliminates the possibility of their premature mechanical damage as in the case of charging a collecting magazine or a cartridge of the prior art stapling devices. The provision of the conduit for feeding the wire to the clamping jaw, and elimination of the necessity to have either a collecting magazine or a cartridge makes it possible to substantially reduce instrument dimensions without any loss in the capacity thereof. Moreover, the factors cited above promote upgrading the reliability of the staple suture, and reducing traumatism in hard-to-access regions of the operative field. An important advantage of the inventive instrument consists in that in order to prepare this instrument for operation, it is sufficiently to insert the wire end into the passage of the clamping jaw (instead of charging a magazine or a cartridge). The preparation time does not practically depend on the size of staples. As against the prior art stapling devices used for suturing, the preparation of the inventive instrument for operation takes 10 to 50 times shorter period of time. Elimination of the need in a magazine or a cartridge permits the weight of the surgical instrument to be reduced, is significant in stomach resection, pneumonectomy, in cardiac-vessel surgery, and in transplantation of organs and tissues.

The inventive surgical instrument may be constructed in the form of scissors or a clip.

In the surgical instrument made in the form of scissors provided with handles and jaws at the ends thereof, it is expedient a modification of the invention wherein a clamping jaw serving as a driver, and a handle rigidly coupled thereto are provided with guides whereon there are mounted said knife and a spring-loaded slide bar having a knurled projection introduced, through a longitudinal slot provided within the clamping jaw, into a passage for feeding the wire the slide bar being coupled with the opposite handle by means of a cam follower, and the passage for feeding the wire nas an outlet end bent toward the female die. This modification is preferable for applying a plurality of single sutures in hard-to-access places of the operative field, e.g. for suturing bronchi and pulmonary tissue, blood vessels, in ophthalmosurgery when applying sutures to ocular tissues, and in neurosurgery. In this case, the role of the staple driver is accomplished by the clamping jaw, and the clamping jaw provided with a curved passage for feeding the wire, the slide bar and the female die act as a device for forming staples. While interacting these elements form an O-shaped staple. An evident additional advantage of the given modification as against the prior art surgical instruments provided with a female die in the form of a hook, lies in that in the given case the clamping jaw and the bearing jaw are holding the tissue being sutured, and in motion toward each other deform the O-shaped staple to such a shape in which it receives only tensile force. This results in a substantial increase in strength and reliability of the suture thus produced. In this modification it is preferred that said guide of the handle be constructed as a cylindrical projection introduced into the guiding groove of the slide bar, while the slide bar be resiliently pressed against the handle by a spring. Such construction provides that the movement of the slide bar, when feeding a wire, and its return into the starting position take place during corresponding working movements of the handles so that additional manipulations are not required.

In order to eliminate auxiliary manipulations it is expedient that in the same modification said knife be kinematically coupled with the slide bar by means of a cylindrical projection fastened on the slide bar and introduced into a transverse guiding slot of the knife.

To carry out microsurgical operations, and to join friable, easily tearing tissues there is preferred a modification of the inventive instrument wherein the bearing jaw carrying the female die is movably couples with the handle by means of a cam gear and has a longitudinal slot into which slot there is introduced a hinge securing said female die, and a projection for periodical interaction with said knife. Such a design of the instrument permits accomplishing stable fixation of a tissue between the jaws until the moment of separating the handles.

From the viewpoint of the design, the simplest is the modification wherein a knurled projection of the spring-loaded slide bar is secured on a resilient element whose one end is rigidly coupled with said slide bar, while the other end thereof is put into contact with a shaped surface of the clamping jaw, the knife and the slide bar being constructed in one piece.

The most universal is the modification of the inventive instrument wherein said cam follower is provided with an extreme position stop, said stop being mounted for displacement to vary the stroke of the handles and of the slide bar, and the angle of opening of the jaws. Since the length of the stroke of the slide bar is proportional to the angle of opening of the handles, this fact permits readjusting the instrument for making the staples of other required size simply by displacing the stop. Such a readjustment can be carried out comparatively rapidly and easily in the course of operation. Said advantage makes it possible to have several multipurpose instruments and 2 to 3 reels of wire instead of a set of numerous specialized instruments. The vital and urgent nature of such a multi-purpose design is evident for medical personnel preparing the operation. A further evident fact lies in that in many cases it is impossible to foresee which stapling instruments, which staples and which number of staples will be required for suturing. At the same time, the success of the whole operation often depends on the rate of suturing.

There is also possible a modification of the instrument in the form of scissors, which modification permits making and applying U-shaped staples. According to this modification, the clamping jaw which serves as a device for forming the staples, is constructed as two levers, the first of said levers being rigidly coupled with the handle and provided with a mandrel at the end thereof, said mandrel being capable of moving from and to the plane of rotation of the jaws, while the second lever is hingedly secured on the first lever, is movably coupled with the handle carrying the bearing jaw provided with the female die, has a U-shaped punch at the end thereof, and carries a L-shaped rotary driver for staples, said knife being secured on the punch, while the passage for feeding the wire is constructed through and straight within the mandrel and the first lever. Such a modification is preferred for opplying staples to form a plurality of single sutures in hard-to-access regions of the operative field. Its advantage is manifested to the best when it is necessary to suture the edges of lacerated wounds since U-shaped ataples ensure greater overlapping the wound than O-shaped staples. The above described modification of the instrument provides for the capacity of from 25 to 30 single staple sutures per minute.

In accordance with the present invention, there is also possible a modification of the surgical instrument in the form of a clip provided with a plurality of staple drivers disposed within the grooves of the clamping jaw, and with a plurality of mating pits disposed within the female die. Such a modification is characterized by that within the clamping jaw there are provided passages for feeding the wire, said passages being orientated perpendicular to corresponding drivers, and each driver being provided with a L-shaped grip, mounted for withdrawal into a recess of the groove, and coupled with the travel actuator, with the said knife constructed in the form of a plurality of blades mounted for reciprocating travel within the grooves of the clamping jaw between the actuators. The given modification of the surgical instrument permits simultaneous forming and applying up to 30 staples, which is often sufficient for the formation of a staple suture along the whole wound. Since the instrument forms the staples from the wire immediately before their being inserted into a tissue, there is no need to accomplish a long-term and labor-consuming preparation of the suturing instrument for operation. The above fact makes it possible to eliminate errors and negative effects which have been considered in detail in the description of the prior art.

It is understood that the actuator for the clamping jaw, the knives and the drivers may be constructed in various forms. However, the simpliest in design is a modification wherein the actuator of the clamping jaw and of the clamping jaw and of the drivers comprises a first stem mounted within the bore of the body, said stem carrying the claming jaw and being provided with guides on which there is mounted a first carriage, a second stem mounted within the bore of the first stem and provided with a conical tip and a collar interacting with the projection of the first carriage, a second carriage mounted on the first carriage for travel across the grooves and pressed by a spring to the extreme position, said carriage being provided with a mating conical opening for said conical tip of the second stem and carrying the drivers and the blades, said blades being provided with through openings mating with the passages for feeding the wire with the knife being in the extreme position.

It is expedient that the blades provided in the clamping jaw be mounted at an angle of 30 to 60° to the axis of the passage for feeding the wire. Such an arrangement provides for the possibility of making staples having sharp ends of the legs thereof. Such staples enter the tissue more easily thereby permitting a force required for displacing the clamping jaw while suturing to be reduced. An important advantage of this modification also consists in that the sharp staples traumatize the tissue to a lesser degree and are not deformed when being inserted thereinto.

There is also possible a modification of the invention wherein the driver grooves and the passages for feeding the wire are orientated at an angle from 30° to 50° to the planes perpendicular to the clamping jaw. A staple suture formed by such an instrument possesses a higher flexibility than the sutures formed by the above considered modifications. The above factor is of particular importance in operations performed on gastroenteric tract and in cardiac-vessel surgery.

There is further possible such a high-capacity modification of a surgical instrument constructed in the form of a clip provided with a staple driver disposed within the groove of the clamping jaw, wherein said staple driver is provided with a L-shaped grip mounted within the groove of the clamping jaw for removal into the recess of said groove, said driver being coupled with the actuator for reciprocating travel and transverse displacement, the female die being constructed as a plate having a series of pits, and being mounted on the guide of the bearing jaw perpendicular to the latter, while a mechanism for index travel of the instrument along said plate is mounted on the body. Such a modification of the instrument provides for rapid application of a lengthy suture at a speed of 60 staples per minute by sequentially applied staples, and is preferred in application of sutures whose length exceeds 10 cm. With such a length of the suture, it is practically impossible to form an even suture, and in particular to maintain constant pitch of the staples when using the above considered modifications.

It is expedient in this modification that the surgical instrument be provided with an adjacent strap provided with a series of bearing sockets, said strap being mounted on said female die in an equidistant position relative to the latter, while the mechanism for index travel be constructed as a rotary lever having a spring-loaded projection at the end thereof, said projection interacting with the bearing sockets of the strap, and with a shaped slot into which slot there is introduced a cylindrical projection coupled with said staple driver actuator.

Such a design embodiment is sufficiently simple and at the same time ensures the constant pitch of the staples. The possibility of replacing the strap and the female die permits forming a suture to a required length.

It is desirable in some cases that said plate and said strap be constructed curvilinear. When having a set of plates and straps of different curvatures, it is possible to easily select them as to their shape of a complicated incision or a wound. Thereby equipped instrument allows staple sutures of practically any configuration to be rapidly formed.

BRIEF DESCRIPTION OF DRAWINGS

The invention is further explained in terms of detailed description of specific embodiments of the surgical instrument with reference to the accompanying drawings in which similar components are designated by similar numerals, and in which:

FIG. 18 shows cross-section of a modification od the clamping jaw provided with a plurality of passages for feeding the wire, said conduits being orientated at an angle to the plane perpendicular to said jaw;

FIG. 20 shows a modification of the instrument constructed in the form of a clip, for rapid formation of a lengthy suture by single staples;

DETAILED EXPLANATION OF THE INVENTION

Figure 1:
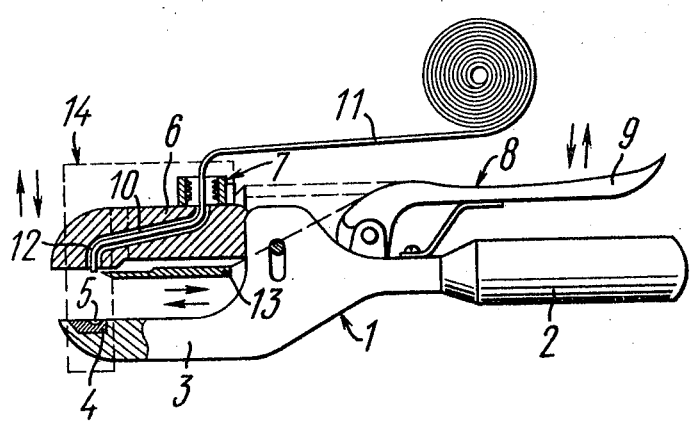
FIG. 1 shows schematically a general view of a surgical instrument for applying of staples.

The inventive surgical instrument for application of staples comprises an elongated body 1 (FIG. 1 of the accompanying drawings) provided with a hand lever 2. At a distal end of said body 1 there is provided a bearing jaw 3 having a female die 4. A pit 5 for bending staples is provided within the female die 4. At the same distal end of the body 1 there is mounted a clamping jaw 6 having a driver 7 for staples. The clamping jaw 6 is mounted on the body 1 for reciprocating travel in the direction toward said female die 4.

The instrument is provided with an actuator 8 for shifting the clamping jaw 6 and the driver 7 for staples. The actuator 8 is movably coupled with the clamping jaw 6 and with the driver 7 for staples. The design of the actuator 8 may be various, e.g. as a hinge-lever mechanism, a cam mechanism, a hydraulic or a pneumatic cylinder etc. For the purpose of illustration, in the given figure the actuator 8 is shown as a rotary lever 9 hingedly mounted on the body 1 in a substantially parallel position relative to the hand lever 2.

According to the invention, within the clamping jaw 6 there is provided a passage 10 for feeding a wire 11. A knife 13 is mounted on the clamping jaw 6 for reciprocating travel in the direction perpendicular to the outlet end 12 of the conduit 10. The knife 13 is designed for cutting off lengths from the wire 11, and is movably coupled with said actuator 8, with the clamping jaw 6, with the staple driver 7, and with the knife 13 which are conditionally shown in dotted lines.

In accordance with the invention, the surgical instrument is provided with a device 14 for forming staples from the wire lengths cut from the wire 11. In the given case, the clamping jaw 6 provided with the passage 10, the female die 4 and the driver 7 for staples function as said device 14.

According to the invention, the proposed surgical instrument for application of staples may be constructed as a conventional clamp having a body 1 in the form of scissors, or as widely known similar instruments provided with the body 1 in the form of a clip.

Figure 2:
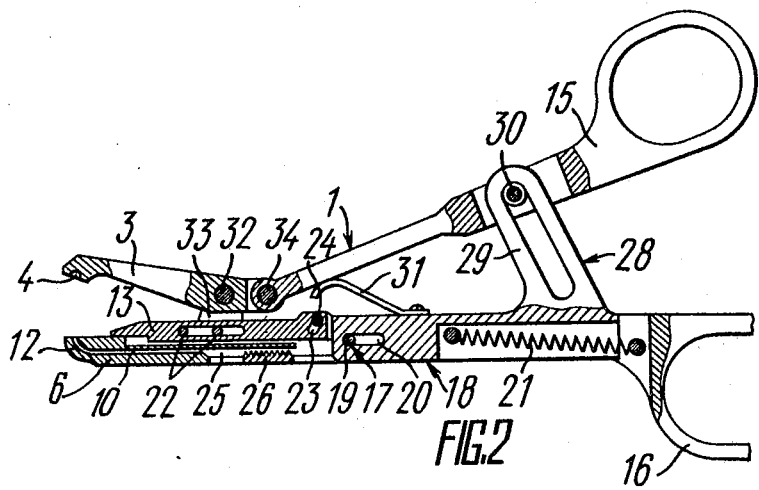
FIG. 2 shows a modification of said instrument in the form of scissors, in a partially cut longitudinal view.

FIG. 2 of the accompanying drawings illustrates one of such modifications of a surgical instrument constructed in the form of scissors provided with handles 15 and 16, and with the clamping jaw 6 and the bearing jaw 3 at the ends thereof. The clamping jaw 6 is rigidly coupled with the handle 16. The handle 16 has a guide 17 on which handle there is mounted a spring-loaded slide bar 18.

Said guide 17 is constructed in the form of a cylindrical projection 19 introduced into a mating guiding groove 20 of the slide bar 18.

In the given modification, the slide bar 18 is resiliently pressed by a tension spring 21 secured to the handle 16. The clamping jaw 6 is provided with a guide 22 on which guide there is mounted the knife 13. In the same modification, in order to eliminate auxiliary operations, the knife 13 is kinematically coupled with the slide bar 18. For this goal, within the knife 13 there is provided a transverse guiding slot 23 into which slot there is introduced a cylindrical projection 24 secured on the slide bar 18.

The passage 10 for feeding the wire is provided with the outlet end 12 bent toward the female die 4. At the inlet to the conduit 10, a longitudinal slot 25 is provided within the clamping jaw 6. The slide bar 18 is provided with a knurled projection 26 introduced into the passage 10 for feeding the wire through the longitudinal slot 25. Between the knurled projection 26 and the slide bar 18 there is provided an opening 27 for inserting the wire end when feeding said wire into the passage 10. The slide bar 18 is coupled with the opposite handle 15 by means of a cam follower 28 which follower in the given case is constructed in the form of a slotted guide plate 29 rigidly secured on the slide bar 18. A freely rotating roller 30 fastened on the handle 15, is introduced into the slot of the slotted guide plate 29. A plate spring 31 is secured on the slide bar 18, said spring thrusting with a free end thereof against the handle 15.

The bearing jaw 3 is constructed in the form of a double-arm lever fastened by means of a cylindrical hinge 32 and a bracket 33 to the handle 16. One arm of the bearing jaw 3 carries the female die 4, while the other end thereof is coupled with the handle 15 by means of a cylindrical hinge 34.

Figure 3:
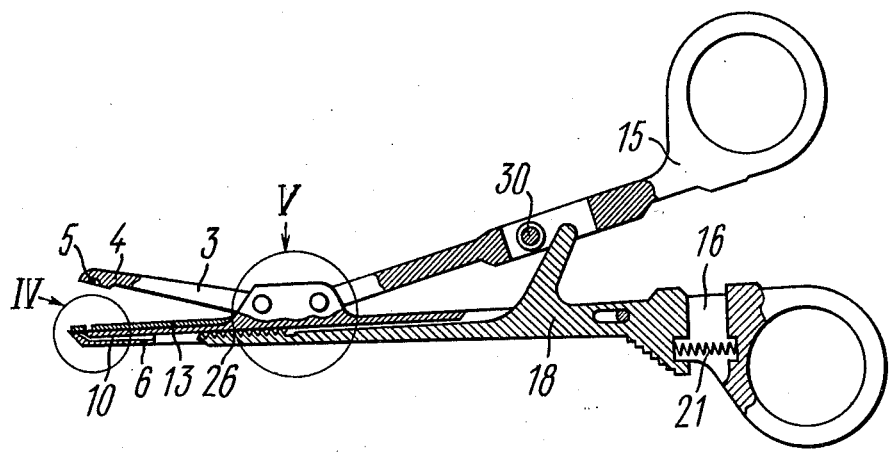
FIG. 3 shows another modification of the instrument in the form of scissors.

The modification of the surgical instrument which is shown in FIG. 3 of the accompanying drawings, is essentially similar to that considered above. However, the knife 13 is kinematically coupled with the bearing jaw 3, while the cam follower 28 is made in the form of an inclined projection 35 which is rigidly secured on the slide bar 18 and interacting with the roller 30 fastened on the handle 15. Moreover, the slide bar 18 is resiliently pressed by means of the spring 21 which is made in the form of a compression spring.

Figure 4:
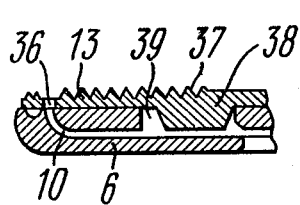
FIG. 4 shows an enlarged view of a clamping jaw and a knife, fragment IV in FIG. 3.

The design of the clamping jaw 6 and that of the knife 13 can be better seen in FIG. 4 of the accompanying drawings in which they are illustrated in an enlarged scale. The knife 13 is provided with a through opening 36 and with a knurled surface 37 facing the female die 4. The knife 13 is further provided with a projection 38 introduced into the passage 10 through a longitudinal slot 39 of the clamping jaw 6.

Figure 5:
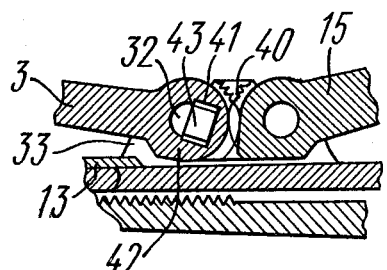
FIG. 5 shows an enlarged view of a bearing jaw provided with a handle, and a knife, fragment V in FIG. 3.

The kinematic link between the knife 13 and the bearing jaw 3 is better illustrated in FIG. 5 of the accompanying drawings in which the fragment V of FIG. 3 is shown in longitudinal section in an enlarged scale. As it can be seen in FIG. 5, the bearing jaw 3 is movably coupled with the handle 15 by means of a cam gear 40.

A longitudinal slot 41 is provided within the bearing jaw 3, into which slot there is introduced the hinge 32 coupled with the bracket 33. The hinge 32 is constructed in the form of a semicylinder. Said longitudinal slot 41 is limited at one end thereof by a cylindrical surface, while the other end thereof is limited by a flat surface. The bearing jaw 3 is provided with a projection 42 for periodical interaction with the knife 13. Within the longitudinal slot 41 of the bearing jaw 3 there is mounted the compression spring 43 thrusting against the flat end of the slot 41 and against the plane of the semicylindrical hinge 32. Thus, the spring 43 constantly presses the bearing jaw 3 to the handle 15.

Figure 6:
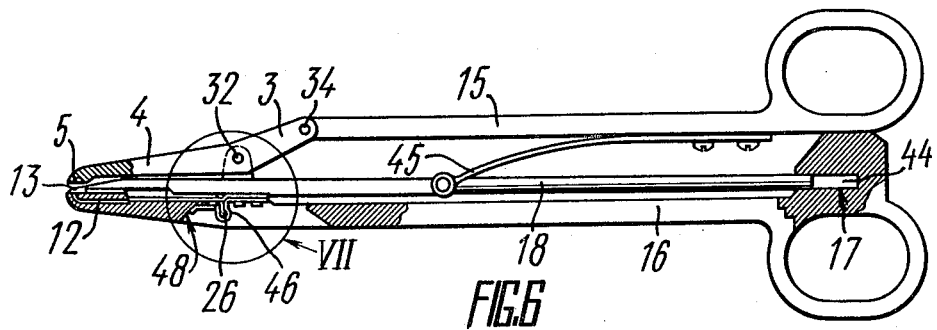
FIG. 6 shows the simpliest modification of the instrument constructed in the form of scissors, partially cut.

More simple in design is the modification of the surgical instrument illustrated in FIG. 6 of the accompanying drawings. The features of this modification consist in the following. The knife 13 and the slide bar 18 are constructed in one piece in the form of a sharp rod. The sharp end of the rod serves as the knife 13, while the opposite end thereof is introduced into an opening 44 of the handle 16, said opening serving as the guide 17. The slide bar 18 is coupled with the handle 15 by the plate spring 45 which spring together with the opening 44 function as said cam follower designated by 28 in FIGS. 2 and 3 of the accompanying drawings. As it can be seen in FIG. 6 of the accompanying drawings, the bearing jaw 3 is constructed as a double-arm lever, while the knurled projection 26 is fastened to the slide bar 18 by means of the resilient element 46.

Figure 7:
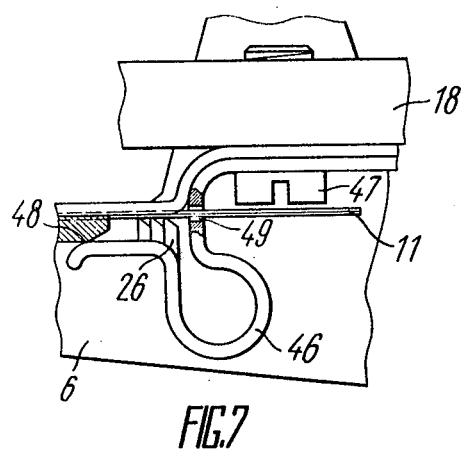
FIG. 7 shows a resilient element provided with a knurled projection, an enlarged view, fragment VII in FIG. 6.

The knurled projection 26 is illustrated in greater detail in FIG. 7 of the accompanying drawings. In this figure it can be seen that one end of the resilient element 46 is rigidly coupled with the slide bar 18 by means of screws 47. The other end of the resilient element 46 is contacted with a shaped surface 48 of the clamping jaw 6. In the resilient element 46 there is provided a through opening 49, the wire 11 being passed therethrough.

Figure 9:
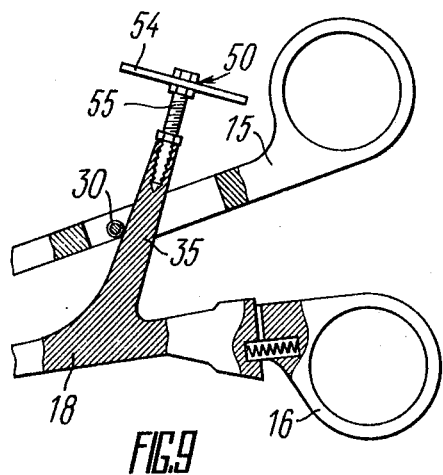
FIG. 9 shows an improvement of the modification shown in FIG. 3.
Figure 8:
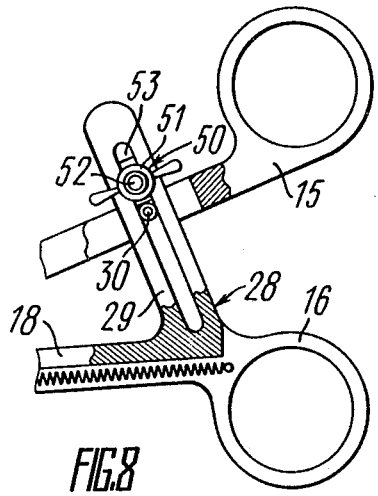
FIG. 8 shows an improvement of the modification shown in FIG. 2.
Figure 10:
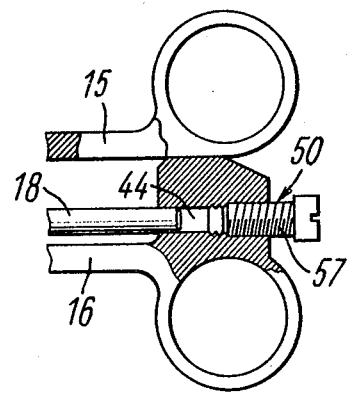
FIG. 10 shows an improvement of the modification shown in FIG. 6.

More perfect versions of the above described modifications of the surgical instrument are shown in FIGS. 8 through 10 of the accompanying drawings.

In accordance with the invention, said cam follower 28 is provided with an extreme position stop 50. The stop 50 is mounted for displacement to vary the stroke of the handles 15 and 16, that of the slide bar 18, and an angle of opening of the jaws 3 and 6 (not shown in FIGS. 8 through 10).

In FIG. 8 of the accompanying drawings, showing an improvement of the modification of the surgical instrument illustrated in FIG. 2, it can be seen that the stop 50 comprises a wing nut 51. The wing nut 51 is screwed on a bolt 52, whose head 53 interacts with the roller 30 fastened on the handle 15. The rod of the bolt 52 is introduced into the slot of the slotted guide plate 29.

FIG. 9 of the accompanying drawings shows an improvement of the modification of the surgical instrument illustrated in FIG. 3 of the accompanying drawings. In the given case, the stop 50 is constructed in the form of a dish-shaped plate 54 fastened on a screw 55 which screw is screwed into the opening of the inclined projection 35. The screw 55 is fixed by means of a lock nut 56. The dish-shaped plate 54 interacts directly with the handle 15, the latter being in the extreme position.

FIG. 10 of the accompanying drawings shows an improvement of the modification of the surgical instrument illustrated in FIG. 6 of the accompanying drawings. In the given case, the stop 50 is constructed in the form of a screw 57 which is screwed into the opening 44 of the handle 16. The end face of the driver 18 introduced into the opening 44, thrusts against the end face of the screw 57 when separating the handles 15 and 16 to a desired angle.

Figure 11:
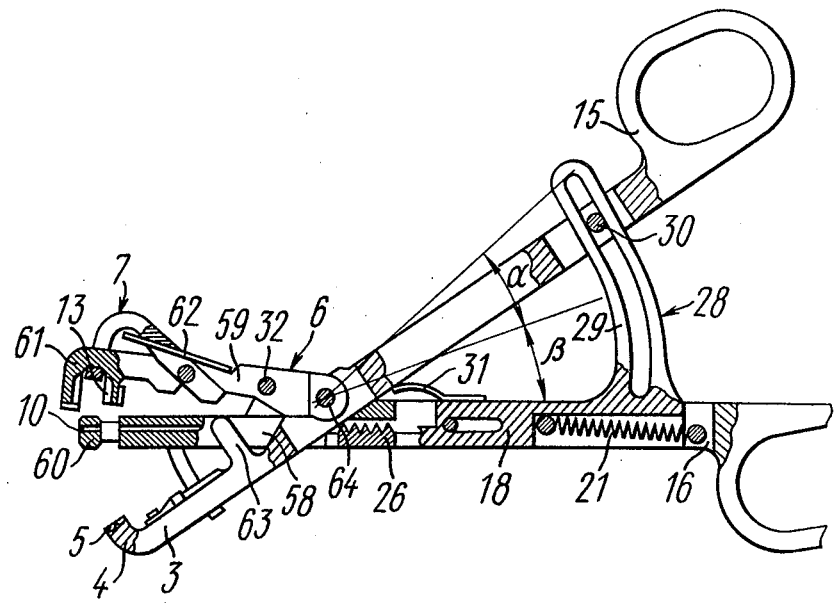
FIG. 11 shows a modification of the instrument constructed in the form of scissors allowing U-shaped staples to be formed.

A modification of the surgical instrument shown in FIG. 11 of the accompanying drawings, like the above considered modifications, is made in the form of scissors. However, this modification permits making and applying U-shaped staples.

According to the invention the clamping jaw 6 serving as the device 14 (see FIG. 1 of the accompanying drawings) for forming staples, is made as two levers 58 and 59. The first lever 58 is rigidly coupled with the handle 16 and is provided with a mandrel 60 at the end thereof. The second lever 59 is fastened by the hinge 32 on the first lever 58 is kinematically coupled with the handle 15 which handle carries the bearing jaw 3 and the female die 4.

The second lever 59 is provided with a U-shaped punch 61 at the end thereof, and carries the driver 7 for staples. The driver 7 for staples is constructed in the form of a L-shaped rotary lever. The L-shaped driver 7 is forced by the plate spring 62 into the extreme position. One end of the L-shaped driver 7 is introduced into the U-shaped punch 61, and the other end interacts with a projection 63 provided on the bearing jaw 3.

The knife 13 is fixed on said U-shaped punch 61. The passage 10 for feeding the wire is made through and straight within the mandrel 60 and the first lever 58. The end of the second lever 59 which end is opposite to the U-shaped punch 61, is coupled with the handle 15 by means of a cylindrical hinge 64.

The slot of the slotted guide plate 29 may be conditionally divided in the longitudinal direction into two portions, the first of which, limited by the angle α, is rectilinear, while the second portion, limited by the angle β, is arched.

The mandrel 60 is mounted for movement from and to the the plane of rotation of the jaws 3 and 6.

Figure 12:
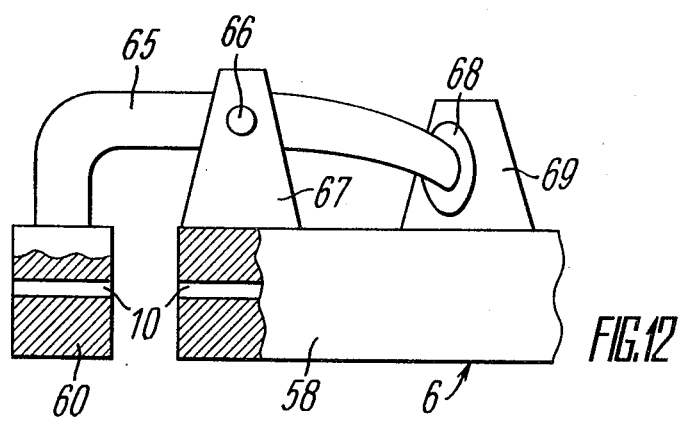
FIG. 12 shows an enlarged view of a mechanism for withdrawing a mandrel, in a view taken along the arrow XII in FIG. 11.

As it can be clearly seen in FIG. 12 of the accompanying drawings, the mandrel 60 is fastened on one end of the double-arm rotary lever 65. The lever 65 is secured to the first lever 58 of the clamping jaw 6 by means of a hinge 66. The other end of the lever 65 is made as a curvilinear cam and is introduced into a guiding opening 68 of a bracket 69. The bracket 69 is fastened on the bearing jaw 3.

Figure 13:
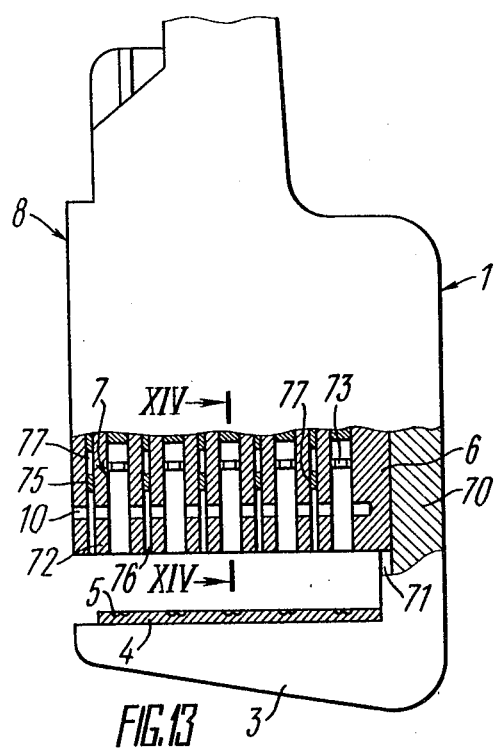
FIG. 13 shows a modification of the instrument constructed in the form of a clip.

More productive is the modification of the inventive surgical instrument provided with the body 1 in the form of a clip 70 (see FIG. 13 of the accompanying drawings). Like the above considered modifications, in the given version of the surgical instrument there is provided the clamping jaw 6 mounted on guides 71 of the clip 70. On the bearing jaw of the clip 70 there is provided the female die 4 having a plurality of pits 5. Opposite the pits 5, in the clamping jaw 6 there are provided grooves 72 in which there are mounted the staple drivers 7.

According to the invention, within the clamping jaw 6 there are provided the passages 10 for feeding the wire. The passages 10 are oriented perpendicular to the staple drivers 7.

The staple drivers 7 are coupled with the actuator 8 for shifting the clamping jaw 6, said actuator further providing for shifting said drivers 7 within the grooves 72.

Figure 14:
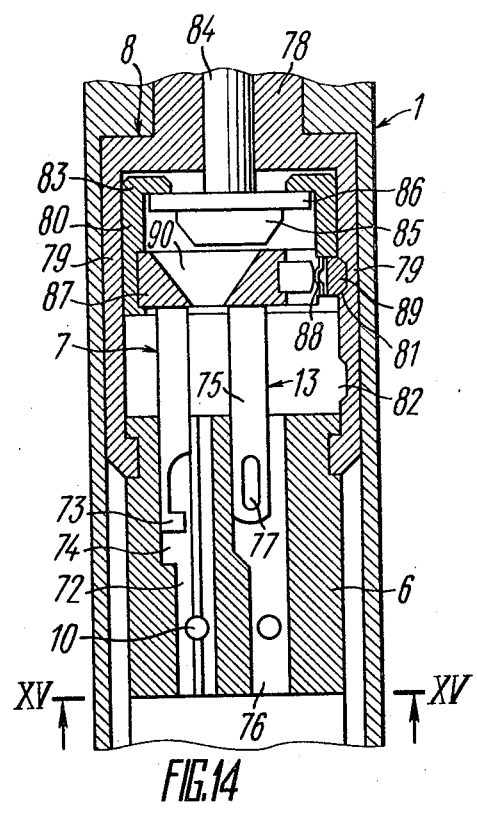
FIG. 14 shows an actuator for travel of the jaw and of the drivers, cross-sectional view.

Each staple driver 7, as it can be well seen in FIG. 14 of the accompanying drawings, is provided with a L-shaped grip 73 in the lower portion thereof, said grip serving together with the walls of the groove 72 as the device 14 for forming the staples. Within the grooves 72 there are provided recesses 74. Said staple drivers 7 are mounted for moving into the recesses 74 of the grooves 72.

The knife 13, as it can be clearly seen in FIGS. 13 and 14 of the accompanying drawings, is made in the form of a plurality of blades 75. The blades 75 are mounted within grooves 76 of the clamping jaw 6 for reciprocating travel between the staple drivers 7.

In the lower portion of each blade 75 there is provided an opening 77 matching the passage 10 when the knife 13 is in the extreme position. A rim bordering the opening 77 is sharpened and functions as a cutting edge.

The simplest in design is the modification of the surgical instrument provided with the actuator 8 illustrated in FIG. 14 of the accompanying drawings. The blade 75 and the staple driver 7 can be simultaneously seen in this figure since in the given case there is shown a surgical instrument for simultaneously forming a double suture consisting of two rows of staples.

The actuator 8 for shifting the clamping jaw 6 and the staple drivers 7 comprises a first stem 78 mounted within the bore of the body 1, said stem carrying the clamping jaw 6 and having guides 79 on which a first carriage 80 is mounted. Within the guides 79 of the first stem 78 there are provided sockets 81 and 82. The first carriage 80 is provided with a projection 83. A second stem 84 is mounted within the opening of the first stem 78, the former being provided with a conical tip 85 and a collar 86. The collar 86 is located under the projection 83 and interacts therewith with its upper surface.

On the first carriage 80 there is mounted a second carriage 87 capable of shifting across the grooves 72 and 76. The second carriage 87 is pressed by a plate spring 88 to the extreme position. The spring 88 thrusts against a latch 89 mounted within a through opening of the first carriage 80 and alternatively introduced into the sockets 81 and 82. The second carriage 87 is provided with a conical opening 90 to match said conical tip 85 of the second stem 84. As it can be seen, the conical opening 90 is slightly displaced to the left relative to the conical tip 85 when the second carriage 87 is in the extreme position. The second carriage 87 carries the staple drivers 7 and the blades 75 of the knife 13.

Figure 15:
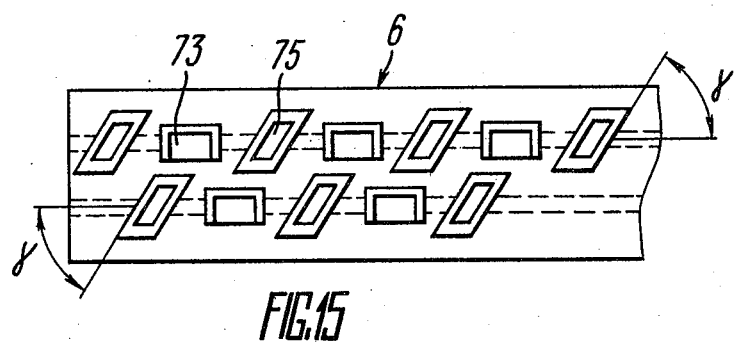
FIG. 15 shows the clamping jaw of the instrument with blades orientated at an angle to a conduit for feeding the wire.
Figure 16:
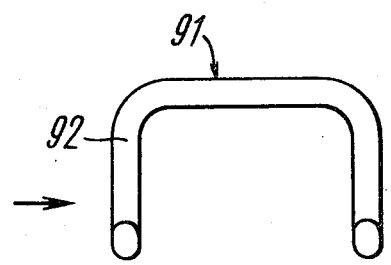
FIG. 16 shows a staple having sharp legs, said staple being made within the clamping jaw shown in FIG. 15.
Figure 17:
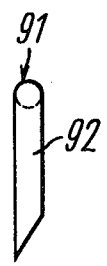
FIG. 17 shows the staple having sharp legs, the view taken along the arrow XVII in FIG. 16.

To provide staples 91 having legs 92 with sharp ends (see FIGS. 16 and 17 of the accompanying drawings) it is expedient that the blades 75 be mounted within the clamping jaw 6 at an angle $\gamma$ of 30° to 60° to the axis of the passage 10 for feeding the wire as it can be well seen in FIG. 15 of the accompanying drawings.

There is also possible the modification of the surgical instrument (see FIG. 18 of the accompanying drawings), wherein the staple drivers 7 and the passages 10 for feeding the wire are oriented at an angle $\phi$ to corresponding planes which are perpendicular to the clamping jaw 6. The angle $\phi$ is selected within the range of 30° to 50°. The blades 75 of the knife 13 in the given case are located at the inlet and at the outlet of the passages 10 for feeding the wire.

Figure 19:
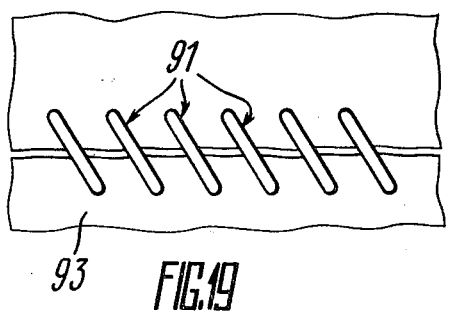
FIG. 19 shows a staple suture applied by means of the clamping jaw shown in FIG. 18.

This modification permits providing a staple suture characterized by the high flexibility and great reliability. The orientation of the staples 91 forming such a suture on a tissue 93 is illustrated in FIG. 19 of the accompanying drawings.

To form elongate staple sutures whose length exceeds 10 cm, a modification of the surgical instrument as shown in FIG. 20 of the accompanying drawings is preferred. In accordance with this modification, the body 1 consists of two portions: the L-shaped bearing jaw 3 and the clamping jaw 6 constructed in one piece with a body 94 of an actuator 95 for reciprocating travel and transverse displacement of the staple driver 7. The L-shaped bearing jaw 3 is provided with a guide 96 mounted on the clamping jaw 6 and forms, together with said guide, the clip 70.

Within the clamping jaw 6 there is provided one groove 72, in which groove there is mounted the staple driver 7 having the L-shaped grip 73. Like in the above considered modifications, the staple driver 7 is mounted for reciprocating travel and removal into the recess 74 of the groove 72. The staple driver 7 is movably coupled with the actuator 95.

According to the invention, on the bearing jaw 3 there is provided a guide 97 whereon the female die 4 is mounted. The female die 4 is constructed in the form of a plate 98 having a row of the pits 5. The plate 98 is mounted in the perpendicular position relative to the bearing jaw 3.

On the body 1, according to the invention, there is mounted a mechanism 99 for index travel of the instrument along said plate 98. A wedge fastener 100 is provided on the body 1, said fastener interacting with the guide 96 of the bearing jaw 3.

The actuator 95 comprises a body 94 wherein there is provided an inlet passage 101. To the inlet passage 101 there is connected a replaceable compressed gas cylinder 102. The inlet passage 101 is communicated via a slide valve 103 with a working chamber 104 provided within the body 94. To the upper end of the slide valve 103 there is fastened a push button 105. The push button 105 is pressed upwards by a spring 106.

The cavity of the working chamber 104 is separated by a resilient membrane 107. A rounded tip of a stem 108 thrusts against the membrane 107. The stem 108 is pressed to the membrane 107 by a conical spring 109. At the opposite end of the stem 108 there is fastened a wedge tip 110 having a cylindrical projection 111. A wedge slide bar 112 is in contact with the wedge tip 110, said slide bar being mounted within the groove 72 of the clamping jaw 6. The wedge slide bar 112 is provided with a groove in which a spring latch 113 is mounted.

Sockets 114 and 115 receiving the latch 113, are provided within the wall of the recess 73.

The above described modification of the surgical instrument is provided with a replaceable strap 116 mounted on the female die 4 in an equidistant position relative to the latter by means of bolts 117. Within the strap 116 above the pits 5 of the female die 4 there are provided through openings 118, a bearing socket 119 being provided next to each opening 118. The openings 118 and the bearing sockets 119 are disposed in parallel rows.

Figure 21:
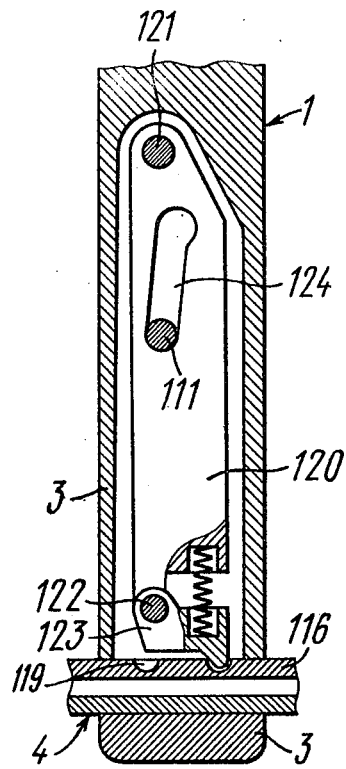
FIG. 21 shows a mechanism for index shifting the instrument.

The mechanism 99 for index travel is constructed in the form of a rotary lever 120 (see also FIG. 21 of the accompanying drawings). The upper end of the rotary lever 120 is fitted on a shaft 121 fastened to the body 1. On the lower end of the rotary lever 120, a spring-loaded projection 123 is fastened by means of a hinge 122, said projection interacting with the bearing sockets 119 of the strap 116. In the middle portion of the rotary lever 120 there is provided a shaped slot 124 into which said cylindrical projection 11 is introduced. The rotary lever 120 is coupled with the actuator 95 of the stape driver 7 via the cylindrical projection 111.

Figure 22:
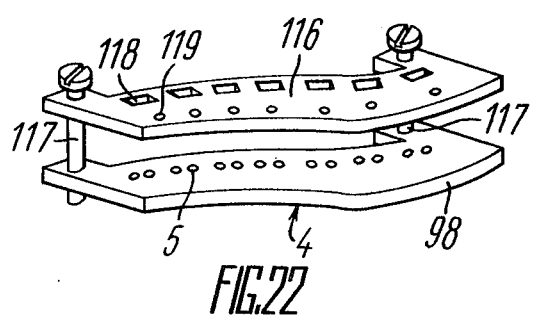
FIG. 22 shows a strap and a plate used for suturing wounds of a complicated configuration.

For rapid formation of elongate staple sutures of a complicated configuration it is expedient that the plate 98 and the strap 116 be constructed curvilinear (see FIG. 22 of the accompanying drawings). In this figure it can be well seen that the strap 116 is coupled with the plate 98 by means of bolts 117. This modification of the surgical instrument is equipped with a set of plates 98 and straps 116 being of various configurations and curvatures.

The above described surgical instrument operates as follows.

The wire 11 is introduced into the passage 10 (see FIG. 1 of the accompanying drawings). The edges of a tissue being joined are introduced into the gap between the clamping jaw 6 and the bearing jaw 3. Following this, the surgeon presses the rotary lever 9. During rotation of the lever 9 being the actuator 8, the clamping jaw 6 shifts towards the bearing jaw 3 while pressing together the edges of the tissue being joined. Simultaneously, the staple driver 7 actuates pushing the end of the wire 11 out of the outlet end 12 of the passage 10. The end of the wire 11 pierces the tissue being joined and, while thrusting against the pit 5 of the female die 4, swings around by 180°. Upon swinging around, the end of the wire 11 again pierces the tissue being joined and under the effect of the staple driver 7, continues its movement towards the clamping jaw 6.

When said end of the wire 11 reaches the outlet end 12 of the passage 10, an O-shaped loop is formed. At this moment, under the action of the rotary lever 9, the knife 13 comes up to the outlet end 12 of the passage 10 and cuts off the formed staple.

The clamping jaw 6 continues approaching the female die 4 under the action of the rotary lever 9, thereby deforming the formed O-shaped staple. Upon finishing formation of a single staple suture, the surgeon releases the rotary lever 9 which lever, while rotating under the action of a reset spring, returns the knife 13, the clamping jaw 6 and the stape driver 7 into the initial position. The process of application of subsequent staples is carried out in a similar way to the described above.

The modification of the surgical instrument illustrated in FIG. 2 of the accompanying drawings operates substantially as herein described. However, some features of operation thereof are to be described in greater detail.

When preparing the instrument for operation, the surgeon introduces the thumb and the forefinger of his right hand into the rings of the handles 15 and 16. Using his left hand, the surgeon introduces the wire through the opening 27 into the passage 10 while beginning to put together the handles 15 and 16 with his right hand. The edges of a tissue to be joined are introduced into the gap between the bearing jaw 3 and the clamping jaw 6. Under the action of the spring 31 while the handles 15 and 16 are being put together, the hinge 34, having passed the equilibrium position, shifts sharply in the upward direction. The bearing jaw 3 rotates towards the clamping jaw 6 thereby pressing the tissue to be joined thereto. As the handles 15 and 16 are further put together, the roller 30 interacts with the slotted guide plate 29 of the cam follower 28, shifting the slide bar 18 in the forward direction and overcoming the force of the tension spring 21.

The knurled projection 26, while interacting with the wire, pushes said wire through the bent outlet end 12 of the passage 10. The wire end pierces the tissue, and the O-shaped loop is formed as above described. In further putting together the handles 15 and 16, and in reciprocating displacement of the slide bar 18, the cylindrical projection 24 pushes the knife 13 in the direction of the outlet end 12 of the passage 10. The knife 13 cuts the formed O-shaped loop off the consumed wire. In the process of putting together the handles 15 and 16 until the stop, the bearing jaw 3 deforms the formed O-shaped loop and finishes the staple formation.

After application of the staple, the surgeon separates the handles 15 and 16. Under the action of the spring 21, the slide bar 18 returns to the right entraining the knife 13. With maximum separation of the handles 15 and 16, the hinge 34 again passes the equilibrium position and the bearing jaw 3, while rotating around the hinge 32, releases the edges of the tissue being sewed. The surgical instrument is ready for application of the next staple.

The modification of the surgical instrument illustrated in FIG. 3 of the accompanying drawings operates substantially as herein described. However, prior to application of a staple it is necessary to separate the handles 15 and 16. In doing so, the slide bar 18 shifts to the left under the action of the compression spring 21. The knurled projection 26, while shifting the wire along the passage 10, pushes the end thereof into the gap between the jaws 3 and 6. The edges of the tissue to be joined are pierced by the end of the wire extending from the passage 10. Following this, the surgeon brings together the handles 15 and 16. The roller 30, while interacting with the inclined projection 35 of the cam follower 28, simultaneously shifts the slide bar 18 to the right. At the same time, the rotation of the handle 15 carried out by means of the cam gear 40 (see FIG. 5 of the accompanying drawings), results in the rotation of the bearing jaw 3 in the direction of the clamping jaw 6 (see FIG. 3 of the accompanying drawings). The pit 5 of the female die 4, while interacting with the loose end of the wire, bends said end and rotates it by 180°. In further rotation of the bearing jaw 3, the end of the wire again pierces the tissue, and having come to the clamping jaw 6, closes the O-shaped loop.

Under the action of the cam gear (see FIG. 5 of the accompanying drawings), the bearing jaw 3 displaces to the left, while overcoming the force of the spring 43. The projection 42 of the bearing jaw 3 pushes the knife 13 to the left as well. The knife 13 cuts the formed staple from the wire and simultaneously pushes out the joined edges of the tissue (see FIG. 3 of the accompanying drawings).

The modification of the inventive surgical instrument shown in FIG. 6 of the accompanying drawings, operates substantially as herein described. In the process of preparation of the surgical instrument for operation, the handles 15 and 16 are separated to the maximum degree. The plate spring 45 removes the slide bar 18 and the knife 13 to the right, while the hinge 34 passes the equilibrium position, and the bearing jaw 3 moves away from the clamping jaw 6. The edges of the tissue being joined are introduced into the gap between the jaws 3 and 6, and the handles 15 and 16 are started to be brought together. In doing so, the plate spring 45 shifts the slide bar and the resilient element 46 to the left. The knurled projection 26 fastened on the resilient element 46 (see also FIG. 7 of the accompanying drawings), interacts with the wire 11 and pushes said wire through the passage 10. The end of the wire 11 comes out of the passage 10, pierces the tissue and bends within the pit 5 of the female die 4, following which said end again pierces the tissue and closes the O-shaped loop.

At this moment, with further bringing together the branches 15 and 16, the knife 13 comes up to the bent outlet end 12 of the passage 10 which knife cuts off the formed staple. At the same moment, the free end of the resilient element 46 crawls onto the shaped surface 48 of the clamping jaw 6 and removes the knurled projection 26 from the contact with the wire 11.

The improved modification of the surgical instrument illustrated in FIG. 8 of the accompanying drawings operates exactly as the modification shown in FIG. 2 of the accompanying drawings. However, if the size of a staple is to be either increased or reduced, the extreme position stop 50 is displaced. For this goal, the butterfly nut 51 is unscrewed, the bolt 52 is shifted along the slot of the slotted guide plate 29 in a desired direction, and is fixed by the butterfly nut 51. Thus the magnitude of the maximum angle of opening of the handles 15 and 16 is changed together with the stroke of the slide bar 18 provided with the knurled projection 26. It is obvious that the length of a blank designed for the formation of a staple depends directly upon the magnitude of the stroke of the slide bar 18.

In the improved modification of the surgical instrument shown in FIG. 9 of the accompanying drawings, the dish-shaped plate 54 thrusting against the handle 15, serves as a limiter for the stroke of the slide bar 18. To vary the magnitude of the stroke of the slide bar 18, it is necessary to release the lock nut 56 and, while turning the screw 55, either to bring the dish-shaped plate 54 nearer to the handle 15, or to remove said plate from said handle. After the adjustment is finished, it is necessary to fix the lock nut 56 again.

In the improved modification of the surgical instrument shown in FIG. 10 of the accompanying drawings, the magnitude of the stroke of the slide bar 18 is adjusted by rotating the screw 57 which screws as the stop 50 and interacts with the end face of the slide bar 18 within the opening 44.

The modification of the surgical instrument illustrated in FIG. 11 of the accompanying drawings operates substantially as herein described. In the starting position, the handles 15 and 16 are separated to the maximum extent. The surgeon introduces the edges of a tissue to be joined into the gap between the bearing jaw 3 and the first lever 58, and starts bringing the handles 15 and 16 together.

In doing so, the roller 30, while interacting with the straight portion of the slotted guide plate 29 within the limits of the angle α, shifts the slide bar 18 to the left. The knurled projection 26 pushes the wire end out of the passage 10 of the first lever 58 and into the passage 10 of the mandrel 60.

The hinge 64 passes the equilibrium position under the action of the plate spring 31, while the second lever 59 approaches the first lever 58. The U-shaped punch 61 embraces the mandrel 60, while the knife 13 cuts the blank off the wire. The U-shaped punch 61, while being pressed to the mandrel 60, forms the U-shaped staple. The roller 30 already moves along the arched portion of the slot of the slotted guide plate 29, said portion being limited by the angle β. Therefore, the slide bar 18 remains immovable, and the wire is not fed.

Under the action of the handle 15 the bearing jaw 3 approaches the first lever 58. In doing so, the bracket 69 (see also FIG. 12 of the accompanying drawings) interacts with the curvilinear cam of the lever 65. The lever 65 rotates around the hinge 66 and removes the mandrel 60 away from the plane of rotation of the jaws 3 and 6. As the bearing jaw 3 moves further it presses the edges of the tissue being joined against the first lever 58 and the U-shaped punch 61. At this moment the projection 63 of the bearing jaw 3 interacts with the end of the L-shaped staple driver 7. The L-shaped driver 7 turns while overcoming the force of the plate spring 62. The second end of the L-shaped driver 7 enters the U-shaped punch 61 and ejects the formed U-shaped staple. The legs of the U-shaped staple pierce the tissue, enter the pits 5 of the female die 4 and get bent. Completely compressed staple is of a B-shaped form. When the handles 15 and 16 are separated all the components of the instrument return to the initial position.

The modification of the surgical instrument illustrated in FIG. 13 of the accompanying drawings operates as follows.

When the clamping jaw 6 is in the extreme upper position, a wire is inserted into the passage 10. The shelves of the L-shaped grips 73 are located under the conduit 10, while the openings 77 of the blades 75 are disposed opposite the outlet openings of the conduits 10. The edges of the tissue to be joined are introduced into the gap between the jaws 3 and 6. Then the staple drivers 7 together with the L-shaped grips 73 and the blades 75 are shifted upwardly. Sharp edges of the blades 75 cut the wire into lengths. The L-shaped grips 73 of the drivers 7 pull said lengths into the grooves 72. In doing so, the lengths acquire the form of the U-shaped staples. Following this, the clamping jaw 6 shifts towards the bearing jaw 3 along the guide 71, while pressing together the ends of the tissue being joined. The drivers 7, while shifting downwardly, eject the formed U-shaped staples out of the grooves 72 by means of the lower end faces of the L-shaped grips 73. The legs of the U-shaped staples pierce the tissue and bend within the pits 5 of the female die 4. Thus, a plurality of staples is simultaneously formed and applied.

The operation of the actuator 8 will become clearer from FIG. 14 of the accompanying drawings. In order to charge the instrument with wire, it is necessary to shift the second stem 84 downwardly. The conical tip 85 of the second stem 84 interacts with the walls of the conical opening 90, and the second carriage 87 shifts to the right while overcoming the resistance of the spring 88. Meanwhile, the latch 89 is introduced into the socket 81.

As the second stem 84 moves further the carriages 80 and 87 go down. Under the action of the first carriage 80 the latch 89 goes out of the socket 81. The drivers 7 with the L-shaped grips 73 and the blades 75 go down together with the second carriage 87. When the shelves of the L-shaped grips 73 are under the passages 10, and the openings of the blades 75 match corresponding passages 10, the latch 89 will enter the socket 82, and the motion will stop. At this moment the wires are introduced into the passages 10.

Following this, the second stem 84 is started being shifted upwardly. The conical tip 85 goes out of the conical opening 90.

The collar 86, while thrusting against the projection 83, shifts the first carriage 80 upwards. Under the action of the first carriage 80, the latch 89 goes out of the socket 82. The second carriage 87, the drivers 7 and the blades 75 shift upwards together with the first carriage 80. In doing so, the blades 75 cut off the blanks, while the L-shaped grips 73 form the U-shaped staples.

Next, under the action of the spring 88, the second carriage 87 shifts to the extreme left-hand position. The drivers 7 together with the L-shaped grips 73 go away into the recesses 74 and continue ascending, while the formed staples remain within the grooves 72. The first carriage 80 continues shifting upwards until the latch 89 enters the socket 81. Following this, the first stem shifts downwards, the whole clamping jaw 6 goes down thereby pressing the edges of the tissue being joined to the female die 4 (see FIG. 13 of the accompanying drawings).

After the clamping jaw 6 has gone down to the lowermost position, the second stem 84 shifts downwards. The conical tip 85 displaces the second carriage 87 to the right, the drivers 7 go out of the recesses 74 and, together with the carriages 80 and 87, shift downwards within the grooves 72. The lower end faces of the L-shaped grips 73 eject the U-shaped staples from the grooves 72, and application of the suture occurs as above described.

The modification of the surgical instrument shown in FIG. 15 of the accompanying drawings operates in a similar way, with the difference that the blades 75 cut the wire into the blanks at an angle α from 30° to 60°. As a result, the formed staples 91 are provided with the legs 92 having sharp ends (see FIGS. 16 and 17 of the accompanying drawings).

The modification of the surgical instrument shown in FIG. 18 of the accompanying drawings operates substantially in the same manner. However, in the process of preparation of this modification for operation it is necessary to insert a plurality of wires into the passages 10. The staple suture being applied by this modification of the instrument has a configuration illustrated in FIG. 19 of the accompanying drawings.

The modification of the surgical instrument illustrated in FIGS. 20 through 22 of the accompanying drawings operates as follows. The edges of a tissue to be joined are placed into the gap between the plate 98 and the strap 116. Following this, the guide 97 of the bearing jaw 3 is introduced under the projection of the plate 98, while the wire is inserted into the passages 10. Using the bolts 117, the plate 98 and the strap 116 are brought together. By releasing the fastener 100, the bearing jaw 3 and the clamping jaw 6 are brought together. In this position said jaws are fastened by the fastener 100.

Under the action of the conical spring 109 the stem 108 shifts upwards. The wedge-shaped tip 110 and the wedge-shaped slide bar 112 coupled therewith are shifted upwards together with the stem 108. The latch 113 goes out of the socket 115. The wedge-shaped slide bar 112 entrains the driver 7 for staples together with the U-shaped grip 73. In the upward motion of the stem 108 the operation of cutting a blank and forming the U-shaped staple occurs similar to that described above.

After the staple has been formed, the push-button 105 is pressed and the inlet conduit 101 is communicated with the working chamber 104. Compressed gas is fed from the cylinder 102 through the slide valve 103 and into the working chamber 104, said gas pressing the membrane 107 and shifting the stem 108 downwards. The driver 7 goes out of the recess 74 and, while going down, ejects the formed U-shaped staple out of the groove 72. The staple passes through the opening 118 provided in the strap 116, the legs of said staple piercing the tissue and being bent within the pits 5 of the female die 4.

The push-button 105 is released, the working chamber 104 is disconnected from the cylinder 102 and is simultaneously communicated with ambient atmosphere (the conduit not shown). Under the action of the conical spring 109 the stem 108, the driver 7 and the knife 13 are drawn up, thereby forming the next staple as above described. The cylindrical projection 111 shifts upwards together with the wedgeshaped tip 110. Having come up to the bent portion of the shaped slot 124, the cylindrical projection 111 forces the lever 120 to be turned by one step. The spring-loaded projection 123 shifts from one bearing socket 119 into another.

In application of the staple sutures having a complicated configuration, there are used curvilinear straps 116 and the plates 98 illustrated in FIG. 22 of the accompanying drawings.

It is to be understood that particular embodiments of the inventive surgical instrument have been described herein. Various modifications may be made in the invention without departing from the spirit and scope thereof as defined in the following claims.

What is claimed is:

1. A surgical instrument for applying staples, comprising:
    an elongated body having a distal end and a hand lever disposed at the end opposite to said distal end of said body;
    a female die secured at said distal end of said body and provided with a pit for bending the legs of said staples;
    a clamping jaw mounted on said body for reciprocating travel in the direction of said female die, and provided with a driver for inserting staples;
    a passage for feeding a wire, said passage being provided in said clamping jaw and having an outlet end;
    a knife for cutting wire lengths, said knife being mounted on said clamping jaw for reciprocating travel in the direction perpendicular to the outlet end of said passage;
    said clamping jaw provided with a first guide for guiding said knife and a second guide for guiding a spring-loaded slide bar having a knurled member extending into said passage for feeding the wire, said slide bar movable toward and away from said outlet end along said second guide in said clamping jaw; and
    a device for forming staples, mounted on said body.

2. A surgical instrument in the form of scissors provided with handles and jaws at the ends thereof as set forth in claim 1, wherein said clamping jaw is connected with the opposite handle by means of a cam follower, and wherein said wire feeding passage has an outlet end bent toward said female die.

3. A surgical instrument as set forth in claim 2, wherein said guide of said handle is constructed in the form of a cylindrical projection introduced into a guiding groove of said slide bar, said slide bar being pressed by a spring against said handle.

4. A surgical instrument as set forth in claim 3, wherein said knife is movably connected with said slide bar by means of a cylindrical projection attached to said slide bar, said projection being introduced into a transverse guiding slot of said knife.

5. A surgical instrument as set forth in claim 3, wherein said bearing jaw carrying said female die is movably coupled with said handle by means of a cam gear and has a longitudinal slot into which slot there are introduced a hinge for securing said jaw, and a projection for periodical interacting with said knife.

6. A surgical instrument as set forth in claim 2, wherein said knurled projection of said spring-loaded slide bar is secured on a resilient element, one end of said element being rigidly coupled with said slide bar and the other end thereof is contacted with a shaped surface of said clamping jaw, said knife and said slide bar being made in one piece.

7. A surgical instrument as set forth in claim 2, wherein said cam follower is provided with an extreme position stop, said stop being mounted for displacement to vary the stroke of said handles and of the slide bar and the angle of opening of said jaws.

8. A surgical instrument in the form of scissors provided with handles and with jaws for applying staples, comprising:
    an elongated body having a distal end and a hand lever disposed at the end opposite to said distal end of said body;
    a female die secured at said distal end of said body and provided with a pit for bending the legs of said staples;
    a clamping jaw mounted on said body for reciprocating travel in the direction of said female die, and provided with a driver for inserting staples;
    a passage for feeding a wire, said passage being provided in said clamping jaw and having an outlet end;
    a knife for cutting wire lengths, said knife being mounted on said clamping jaw for reciprocating travel in the direction perpendicular to the outlet end of said passage;
    a device for forming staples, mounted on said body;
    said clamping jaw serving as said device for forming staples and said instrument constructed as two levers, a first said lever being rigidly coupled with said handle and having a mandrel at the end thereof mounted for movement from and to the plane of rotation of said jaws, and a second said lever hingedly secured to first said lever and movably coupled with said handle carrying said bearing jaw with said female die, said second handle having a U-shaped punch at its end and carrying an L-shaped rotary staple driver;

said knife being secured on said punch, and said passage for feeding the wire is constructed through and straight within said mandrel and the first lever.

9. A surgical instrument for applying staples, comprising:
- an elongated body having a distal end and a hand lever disposed at the end opposite to said distal end of said body;
- a female die secured at said distal end of said body and provided with a pit for bending the legs of said staples;
- a clamping jaw mounted on said body for reciprocating travel in the direction of said female die, and provided with a driver for inserting staples;
- a passage for feeding a wire, said passage being provided in said clamping jaw and having an outlet end;
- a knife for cutting wire lengths, said knife being mounted on said clamping jaw for reciprocating travel in the direction perpendicular to the outlet end of said passage;
- a device for forming staples, mounted on said body;
- said instrument being in the form of a clip having a plurality of staple drivers, said staple drivers positioned within grooves of said clamping jaw, and a plurality of mating pits in said female die;
- said passages for feeding the wire provided within said clamping jaw being oriented perpendicular to corresponding said drivers, each said driver having an L-shaped grip, and being mounted for withdrawal into a recess of said groove and coupled with an actuator for travel;
- said knife constructed as a plurality of blades mounted for reciprocating travel within grooves of said clamping jaw between said drivers.

10. A surgical instrument as set forth in claim 9, wherein said actuator of said clamping jaw and said drivers comprises a first stem mounted within the bore of said body said stem carrying said clamping jaw and having guides on which guides there is mounted a first carriage, a second stem mounted within the bore of said first stem and having a conical tip and a collar interacting with a projection of said first carriage, a second carriage mounted on said first carriage for travel across said grooves, said second carriage being pressed by a spring to the extreme position, having a mating conical bore to receive said conical tip of said second stem, and carrying said drivers and said blades of said knife, said blades being provided with through openings coinciding with said conduits for feeding the wire with said knife being in the extreme position.

11. A surgical instrument as set forth in claim 9, wherein said blades are mounted in said clamping jaw at an angle of 30° to 60° to the axis of said passage for feeding the wire.

12. A surgical instrument as set forth in claim 9, wherein said drivers and said conduits for feeding the wire are orientated at an angle of 30° to 60° to the planes perpendicular to said clamping jaw.

13. A surgical instrument for applying staples, comprising:
- an elongated body having a distal end and a hand lever disposed at the end opposite to said distal end of said body;
- a female die secured at said distal end of said body and provided with a pit for bending the legs of said staples;
- a clamping jaw mounted on said body for reciprocating travel in the direction of said female die, and provided with a driver for inserting staples;
- a passage for feeding a wire, said passage being provided in said clamping jaw and having an outlet end;
- a knife for cutting wire lengths, said knife being mounted on said clamping jaw for reciprocating travel in the direction perpendicular to the outlet end of said passage;
- a device for forming staples, mounted on said body;
- said instrument being in the form of a clip provided with said staple driver within a groove of said clamping jaw;
- said staple driver being provided with an L-shaped grip;
- said driver being mounted within said groove of said clamping jaw and being adapted for withdrawal into the recess of said groove and being coupled with said actuator for reciprocating travel and transverse displacement;
- said female die being constructed in the form of a plate provided with a number of said pits, said plate being mounted on a guide of said clamping jaw perpendicular to the latter; and
- a mechanism mounted on said body for index travel of the instrument along said plate.

14. A surgical instrument as set forth in claim 13, provided with a removable strap having a series of bearing sockets, said strap being mounted on said female die in an equidistant position relative to the latter, while said mechanism for index travel is constructed as a rotary lever having a spring-loaded projection at the end thereof interacting with said bearing sockets of said strap, and a shaped slot into which is introduced said cylindrical projection connected with said actuator of said staple driver.

15. A surgical instrument as set forth in claim 14, wherein said plate and said strap are made curvilinear.

* * * * *